(12) United States Patent
Zelinsky

(10) Patent No.: US 8,919,206 B2
(45) Date of Patent: Dec. 30, 2014

(54) METHOD OF TESTING SEAL LIP BOND STRENGTH TO METAL SUBSTRATE AND APPARATUS THEREFOR

(75) Inventor: Gene Zelinsky, Ypsilanti, MI (US)

(73) Assignee: Federal-Mogul Corporation, Southfield, MI (US)

( * ) Notice: Subject to any disclaimer, the term of this patent is extended or adjusted under 35 U.S.C. 154(b) by 222 days.

(21) Appl. No.: 13/359,721

(22) Filed: Jan. 27, 2012

(65) Prior Publication Data
US 2012/0192638 A1   Aug. 2, 2012

Related U.S. Application Data

(60) Provisional application No. 61/436,810, filed on Jan. 27, 2011.

(51) Int. Cl.
*G01N 3/08* (2006.01)
*G01N 19/04* (2006.01)

(52) U.S. Cl.
CPC . *G01N 19/04* (2013.01); *G01N 3/08* (2013.01)
USPC .......................................... 73/827; 73/150 A

(58) Field of Classification Search
CPC ................................ G01N 3/08; G01N 19/04
USPC ................ 73/827, 826, 828, 796, 806, 150 A
See application file for complete search history.

(56) References Cited

U.S. PATENT DOCUMENTS

| | | | |
|---|---|---|---|
| 2,959,957 A | 2/1959 | Smith | |
| 3,188,855 A | 6/1965 | Dega | |
| 3,196,670 A | 7/1965 | Lander, Jr. | |
| 3,286,512 A | 11/1966 | Jagger et al. | |
| 3,447,361 A | 6/1969 | Schmidt | |
| 3,580,061 A | 5/1971 | Neuman et al. | |
| 3,724,265 A * | 4/1973 | LaValle | 73/827 |
| 3,987,663 A | 10/1976 | Repella | |
| 4,122,705 A | 10/1978 | Rober | |

OTHER PUBLICATIONS

Ch 2: "Elastomeric Materials for Radial, Lip Seals", In: Horve, Leslie: "Shaft Seals for Dynamic Applications", Jun. 12, 2006, aRC Press, XP002684074, ISBN: 978-0-8247-9716-4, paragraph [2.3.7].*

Horve, L., Ch. 2: "Elastomeric Materials for Radial Lip Seals" In: "Shaft Seals for Dynamic Applications," Paragraph 2.3.7, Jun. 12, 1996, CRC Press, ISBN: 978-0-8247-9716-4.

International Search Report PCT/US2012/022845 mailed on Oct. 11, 2012.

* cited by examiner

*Primary Examiner* — Yuanda Zhang
*Assistant Examiner* — Sheikh Maruf
(74) *Attorney, Agent, or Firm* — Robert L. Stearns; Dickinson Wright, PLLC

(57) ABSTRACT

A method of testing one of bond or fatigue strength of an elastomeric seal lip to a metal substrate and apparatus therefor is provided. The method and apparatus avoid causing inadvertent damage to the seal lip during testing. Further, the method and apparatus allow a tensile force to be applied along an axis of the seal lip along which the seal lip extends regardless of the angle of inclination of the seal lip relative to a central axis of a metal substrate to which the seal lip is attached. Accordingly, accurate and repeatable test results indicating one of bond strength of the seal lip to the metal substrate or fatigue strength of the seal lip are obtained via the method and apparatus.

6 Claims, 7 Drawing Sheets

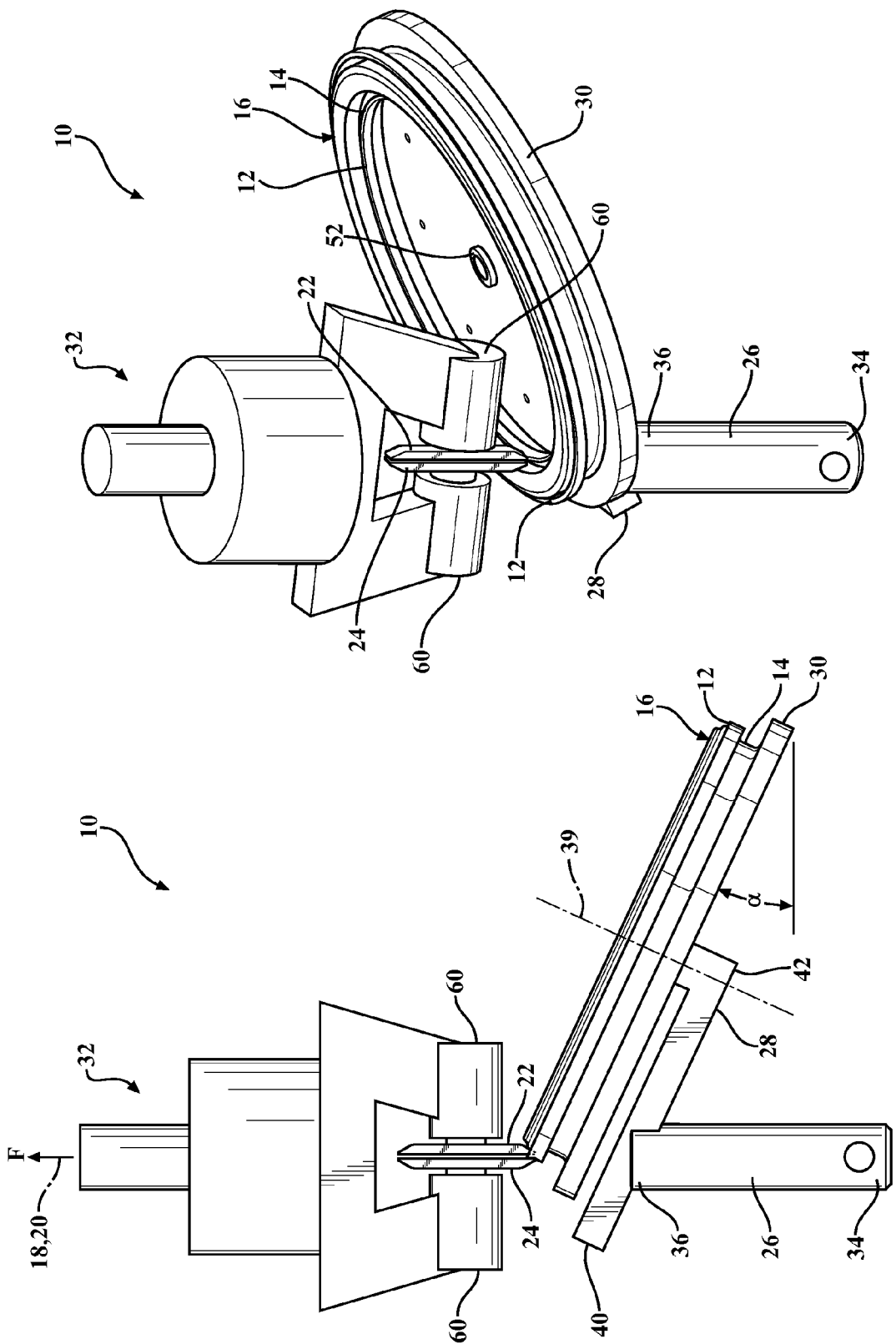

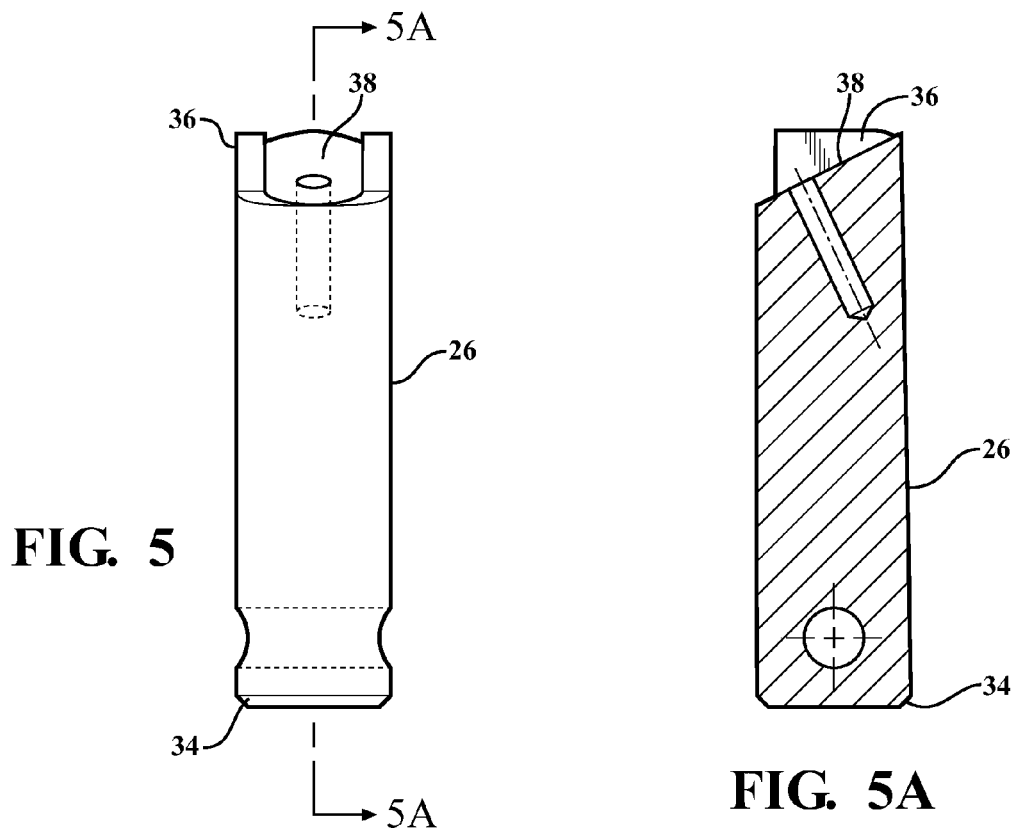
FIG. 5
FIG. 5A
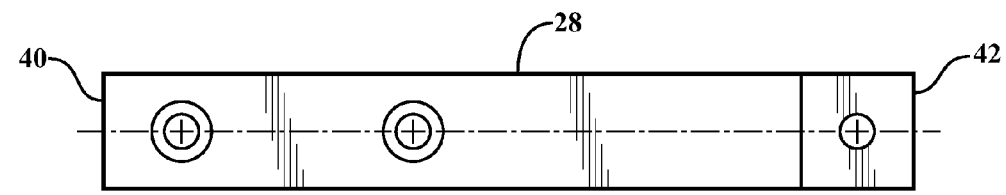
FIG. 6
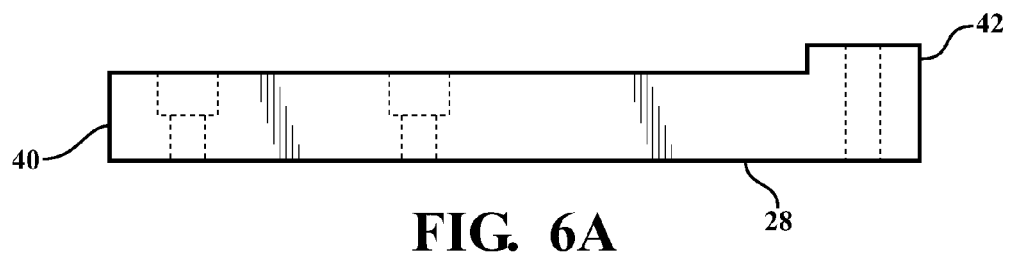
FIG. 6A

FIG. 7
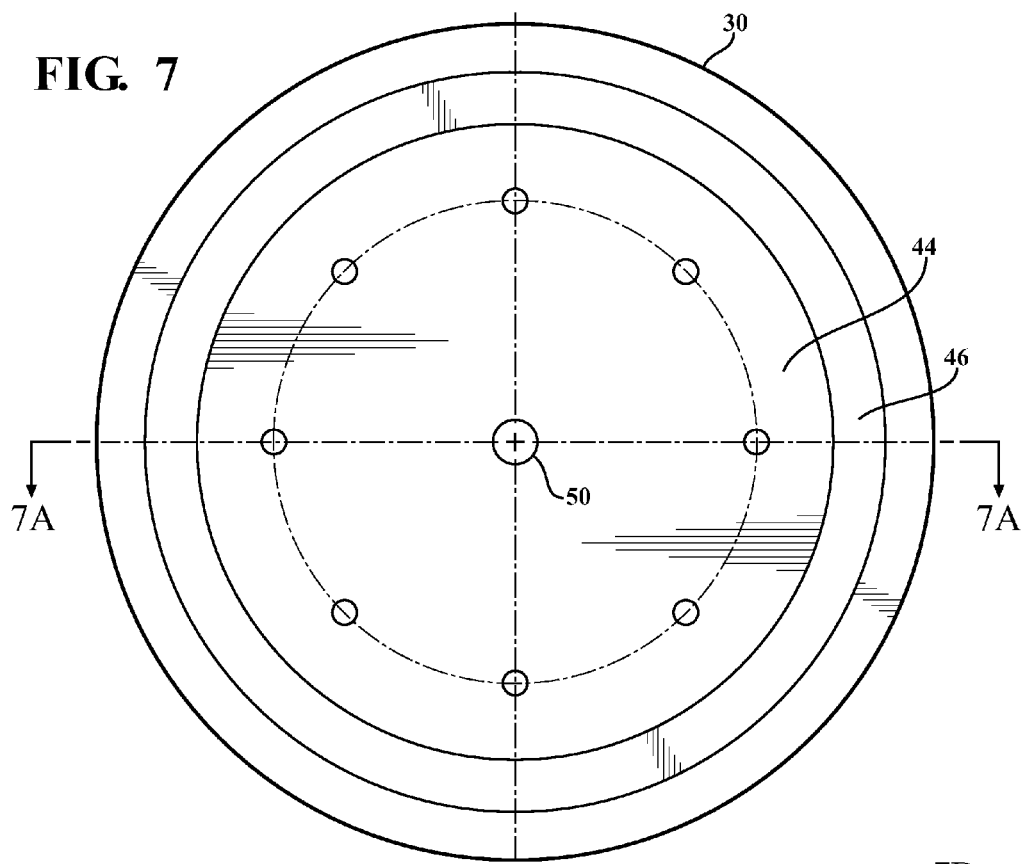
FIG. 7A
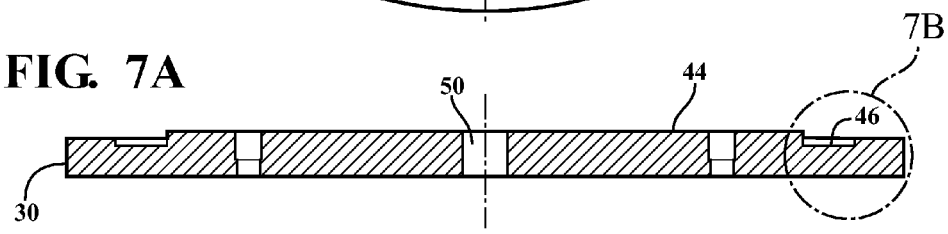
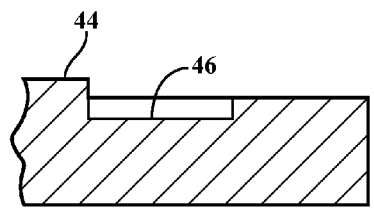
FIG. 7B

METHOD OF TESTING SEAL LIP BOND STRENGTH TO METAL SUBSTRATE AND APPARATUS THEREFOR

CROSS-REFERENCE TO RELATED APPLICATION

This application claims the benefit of U.S. Provisional Application Ser. No. 61/436,810, filed Jan. 27, 2011, which is incorporated herein by reference in its entirety.

BACKGROUND OF THE INVENTION

1. Technical Field

This invention relates generally to elastomeric seal lips bonded to metal substrates, and more particularly to methods of testing the bond strength of an elastomer seal lip to a metal substrate and test fixtures therefor.

2. Related Art

It is known to bond elastomeric seal lips to metal substrates in the construction of seals. This is typically the mechanism used to construct pistons for use in automatic transmissions. It is important while constructing the piston to ensure that the elastomeric seal lip is reliably bonded to the metal substrate of the piston to ensure the seal lip functions as intended in use. Accordingly, empirical testing is commonly performed in an effort to ensure the seal lip is being bonded to the desired specification.

Known testing mechanisms used to determine if a seal is properly bonded to the metal substrate are generally crude and provide test values of marginal repeatability and accuracy. The ability to obtain accurate and reliable test results is complicated due to the fact that the seal lip being tested can be difficult to grasp without causing damage to the seal lip, which in turn affects the accuracy of the test results. This is particularly troublesome when the seal lip is inclined in an oblique relation relative to a central axis of the seal. During testing it is important to grasp the seal lip in a manner that does not impact the ability to obtain reliable test results. As such, the mechanism used to grasp the seal lip must not over compress the seal lip, or the integrity of the seal lip could be compromised, e.g. initiation of a tear, thereby resulting in inaccurate tensile strength test results. In addition, the mechanism used to grasp the seal lip must not under compress the seal lip, or the mechanism will slip off the seal lip without obtaining true tensile strength results of the bond strength. Accordingly, great care must be taken during testing to ensure reliable and accurate test results are being obtained.

SUMMARY OF THE INVENTION

In accordance with one aspect of the invention, a method of testing a seal lip bond strength to a metal substrate is provided. The method avoids causing inadvertent damage to the seal lip during testing. Further, the method allows the tensile force to be applied along an axis of the seal lip along which the seal lip extends regardless of the angle of inclination of the seal lip relative to a central axis of a metal substrate to which the seal lip is attached. Accordingly, the method of testing the bond strength of the seal lip to the metal substrate in accordance with the invention, and fixture therefor, provides accurate and reliable test results for the bond strength of the seal lip to the metal substrate.

The method of testing the bond or fatigue strength of a seal lip on a metal substrate includes: providing a seal assembly having a metal substrate with an elastomeric seal lip bonded thereto; operably fixing the seal assembly to a support plate and orienting a seal lip axis along which the seal lip extends to extend along a predetermined axis; clamping the seal lip between pair of clamping fingers without causing damage to the seal lip; and pulling the seal lip with a force imparted by the clamping fingers along the predetermined axis until the seal lip either separates from the metal substrate or tears.

In accordance with another aspect of the invention, an apparatus for testing the bond and/or fatigue strength of a seal lip is provided. The apparatus includes a tensile pulling mechanism and a pair of clamping finger having opposite free ends and a coupler member between the free ends. The couple member is operably attached to the tensile pulling mechanism. The clamping fingers have clamping surfaces adjacent at least one of their free ends and raised surfaces extending between the clamping surfaces and the coupler member. The clamping surfaces are recessed a first distance relative to the raised surfaces with the raised surfaces being free to abut one another upon the clamping fingers being clamped fully toward one another with the recessed clamping surfaces remaining laterally spaced from one another by a second distance that is two times the first distance.

BRIEF DESCRIPTION OF THE DRAWINGS

These and other aspects, features and advantages of the present invention will become more readily appreciated when considered in connection with the following detailed description of presently preferred embodiments and best mode, appended claims and accompanying drawings, in which:

FIG. 1 is a schematic side view of a seal lip bond strength test apparatus in an outside lip pull configuration constructed in accordance with one aspect of the invention with a seal disposed thereon;

FIG. 2 is a schematic perspective view of the apparatus in an inside lip pull configuration;

FIG. 5 is a front view of a support stud of the apparatus of FIGS. 1 and 3;

FIG. 5A is a cross-sectional view taken generally along the line 5A-5A of FIG. 5;

FIG. 6 is a front view of a tensile frame arm of the apparatus of FIGS. 1 and 3;

FIG. 6A is a side view of the tensile frame arm of FIG. 6;

FIG. 7 is a front view of a support plate of the apparatus of FIGS. 1 and 3;

FIG. 7A is a cross-sectional view taken generally along the line 7A-7A of FIG. 7;

FIG. 7B is an enlarged partial view of the encircled area of FIG. 7A;

DETAILED DESCRIPTION OF PRESENTLY PREFERRED EMBODIMENTS

Figure 10:
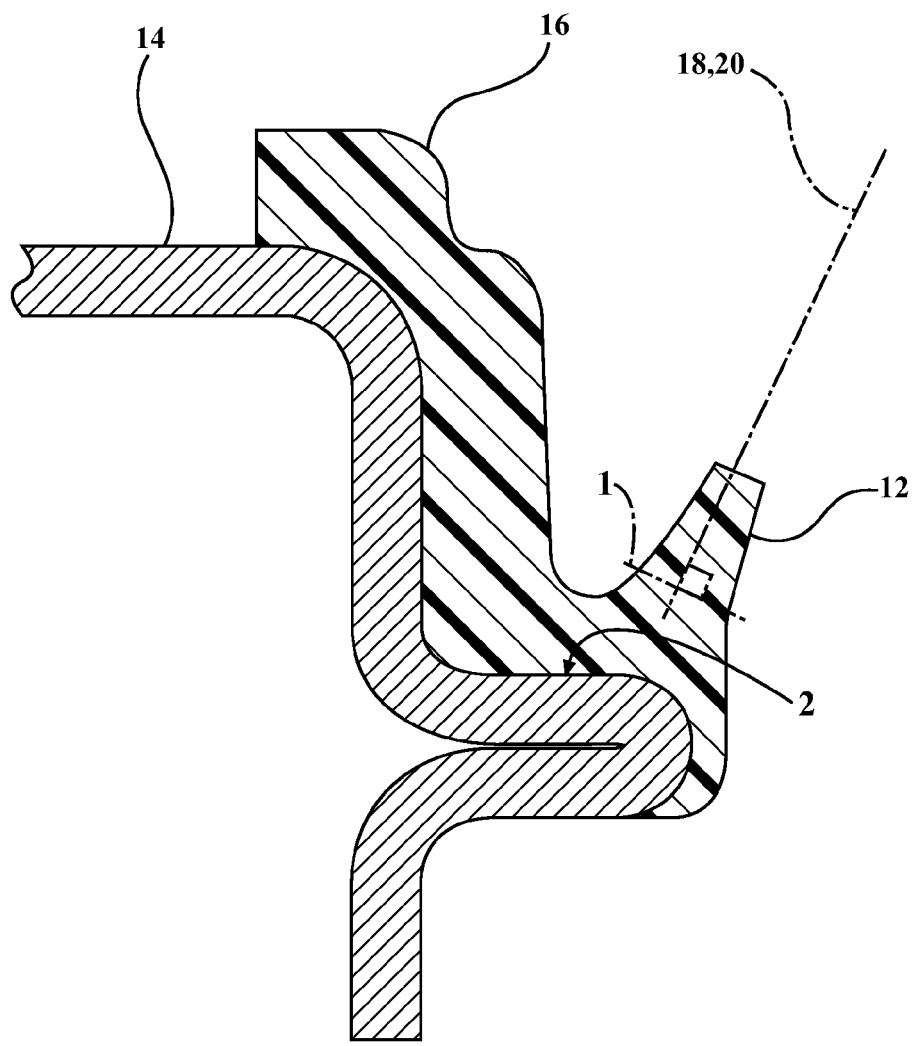
FIG. 10 is a partial schematic cross-sectional view of a seal lip to be tested.

Referring in more detail to the drawings, FIGS. 1-4 illustrate a seal lip bond strength test apparatus, referred to hereafter simply as apparatus 10, constructed in accordance with one aspect of the invention. The apparatus 10 is used to reliably and accurately test the bond strength of an elastomeric (e.g. rubber) seal lip 12 to a substrate, such as a metal case 14 of a seal assembly, e.g. radial shaft, static seal assembly, or piston seal for an automatic transmission, referred to hereafter as seal 16. The apparatus 10 allows the seal 16 to be positioned at a precise angle a of inclination relative to horizontal, which in turn allows a tensile pulling force F to be applied along a pulling axis 18 that is collinear with a seal lip axis 20 along which the seal lip 12 extends (see FIG. 10 for axes 18, 20). Further, the apparatus has a pair of grip fingers, also referred to as clamping fingers 22, 24, that apply a uniform clamping pressure to opposite sides of the seal lip 12 without over compressing and damaging the seal lip 12. Accordingly, clamping fingers 22, 24 configured in accordance with the invention allow tensile force test results to be obtained that are reliable, and that do not reflect undesirable influence from the apparatus 10.

The apparatus 10 includes a support stud 26, a tensile frame arm, also referred to as support arm 28, a seal support member, also referred to as support plate 30, and a pulling member 32 fixed to the clamping fingers 22, 24 to facilitate imparting the tensile force F to the seal lip 12.

The support stud 26 is configured at one end 34 for attachment to a fixed support base 35 and is configured at an opposite end 36 for attachment to the support arm 28. When fixed to the support base 35, the support stud 26 extends generally along the pulling axis 18. As best shown in FIGS. 5 and 5A, the end 36 configured for attachment to the support arm 28 has an end surface 38 inclined relative to the pulling axis 18 to facilitate orienting the support plate 30 in the desired plane oblique to the pulling axis 18, wherein the plane extends along the desired degree angle of inclination, (90-α), relative to the pulling axis 18. Accordingly, the seal lip 12 is readily positioned so that the seal lip axis 20 of the seal lip 12 extends collinearly with the pulling axis 18, while a central axis 39 of the seal 16 extends in oblique relation to the seal lip axis 20.

The support arm 28 is configured adjacent one end 40 for attachment to the end 36 of the support stud 26 and is configured at an opposite end 42 for attachment to the support plate 30. When fixed to the support stud 26, the support arm 28 extends generally upwardly from the support stud 26 along the angle a of inclination. The support arm can be configured in a manner to align the inside lip or outside lip in the correct location to be aligned with axis 18 for application of the tensile force F.

The support plate 30 is shown as being an annular plate having an outer diameter at least slightly greater than the outer diameter of the seal/piston to be supported. To facilitate fixing the seal 16 to the support plate 30, as best shown in FIGS. 7-7B, a surface 44 of the support plate 30 to which the seal 16 is fastened has an annular recessed surface 46 formed therein. The recessed surface 46 is sized to receive the seal 16, and in particular, the case 14 of the seal 16 at least partially therein. To further facilitate attaching the seal 16 to the support plate 30, one or more clamping members 48 (FIG. 4) can be used to clamp the seal 16 in fixed relation to the support plate 30.

The support plate 30 is fixed to the end 42 of the support arm 28 such that the surface 44 of the support plate 30 extends generally co-planar or parallel with the support arm 28 along the angle (90-α) of inclination relative to the pulling axis 18. Accordingly, when the seal 16 is fixed to the support plate 30, the seal 16 is maintained in an inclined orientation along a predetermined angle (90-α) of inclination relative to the pulling axis 18. With the seal 16 fixed and maintained in this predetermined inclined orientation, the seal lip axis 20 of the seal lip 12 being tested extends generally collinearly along the vertical pulling axis 18. The support plate 30 is shown in FIGS. 7 and 7A as having a central aperture 50 to facilitate fixing the support plate 30 to the support arm 28, such as via a threaded fastener 52 (FIGS. 2 and 4), for example. It should be recognized that the components 26, 28, 30 can be fixed to one another via any suitable fastening or joining mechanism, including threaded fasteners or weld joints, for example.

Figure 4:
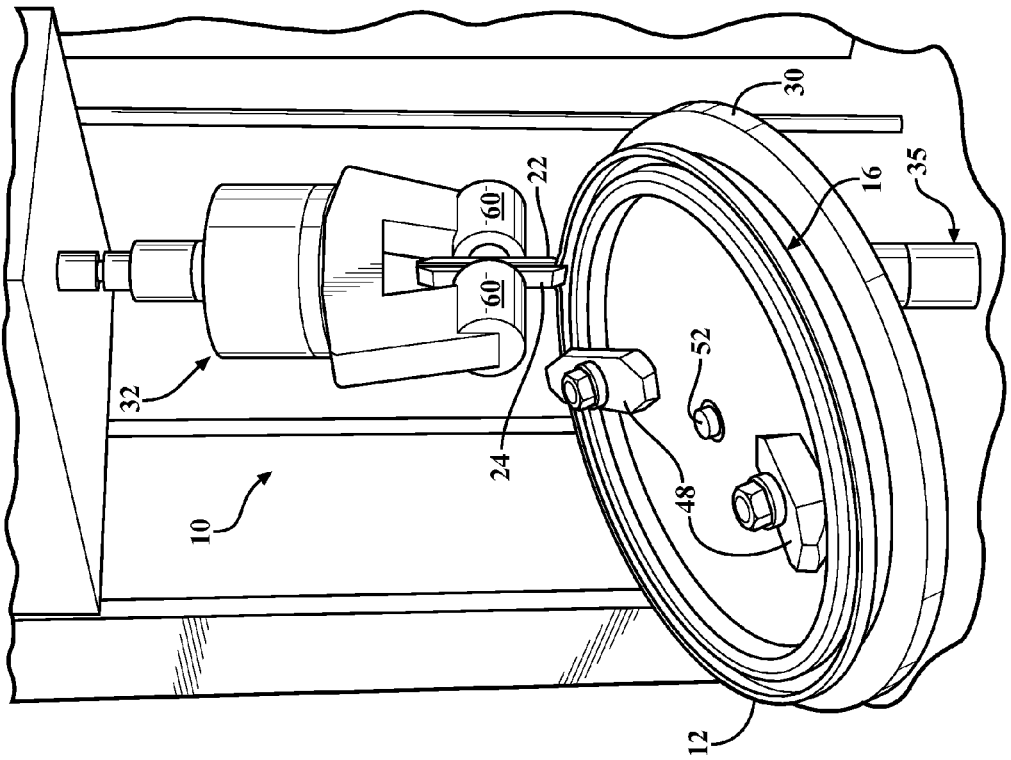
FIG. 4 illustrates an outside lip pull orientation, similar to FIG. 1, showing a view similar to FIG. 3 shown from a different perspective.
Figure 3:
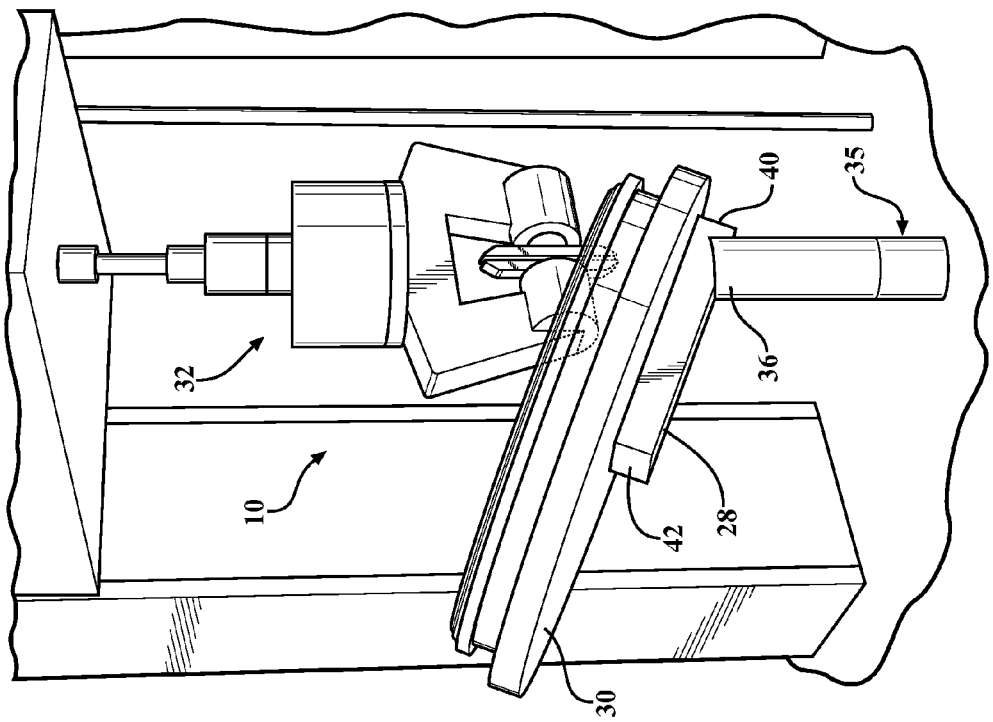
FIG. 3 illustrates an inside lip pull orientation, similar to FIG. 2, showing another perspective view of an apparatus constructed in accordance with the invention with a seal disposed thereon.
Figure 8:
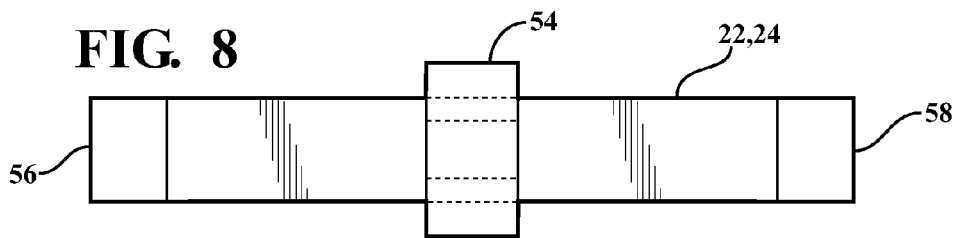
FIGS. 8 and 8A-8B are orthographic views of a grip finger of the apparatus of FIGS. 1 and 3.
Figure 8A:
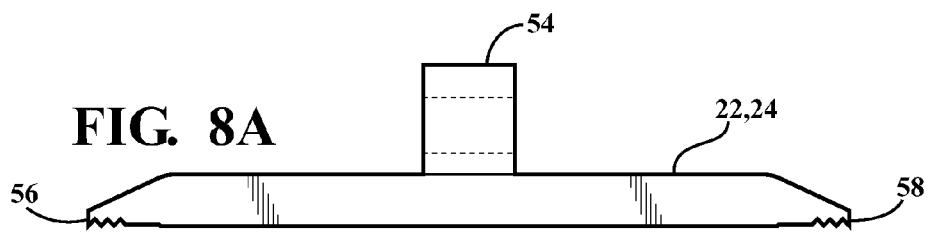
Figure 8C:
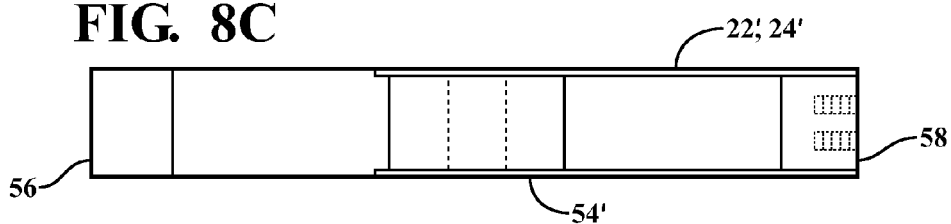
FIGS. 8C and 8D are orthographic views showing an alternate construction of a grip finger of the apparatus of FIGS. 1 and 3.
Figure 8D:
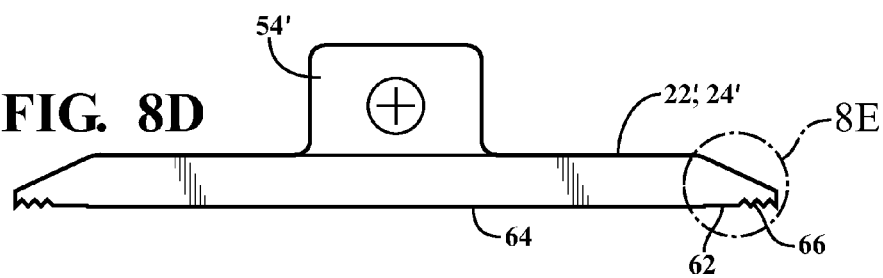

The fingers 22, 24 are shown as being attached or coupled to the pulling member 32 for relative lateral movement toward one another into clamping/gripping relation with the seal lip 12 and away from one another to receive and release the seal lip 12. To facilitate attaching the fingers 22, 24 to the pulling member 32, each finger 22, 24 has a raised coupler portion 54 (FIGS. 8, 8A, 8B, 9, 9A), 54' (FIGS. 8C, 8D) located generally centrally between opposite free ends 56, 58 of the fingers 22, 24. The difference in the coupler portions 54, 54' shown is primarily with their direction of extension, with the couplers 54 shown extending transversely to the length of the fingers 22, 24 and the couplers 54' shown extending along the length of the fingers 22', 24'. The difference in orientation of the coupler portions 54, 54' provides different mechanisms for attachment to the pulling member 32, however, they do not affect how the fingers 22, 24, 22', 24' function in use. Regardless, the coupler portions, discussed hereafter with reference to the coupler portions 54, are configured for releasable attachment to moveable plunger members, also referred to as piston members or pistons 59 for movement in response to actuation of the moveable plungers/pistons slidably received in a housing 60 of the piston members 59.

Figure 8E:
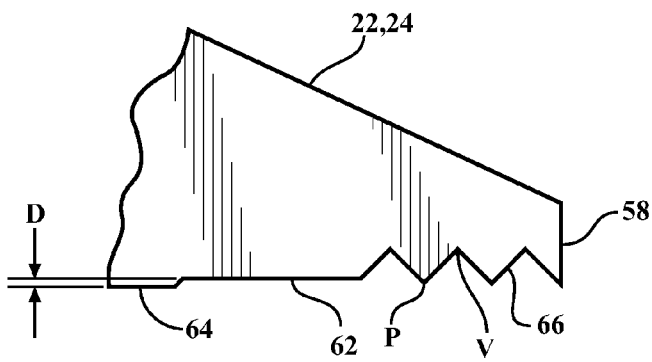
FIG. 8E is an enlarged partial view of the encircled area of FIG. 8D.
Figure 8B:
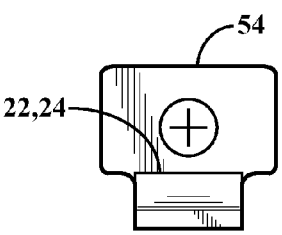
Figure 9A:
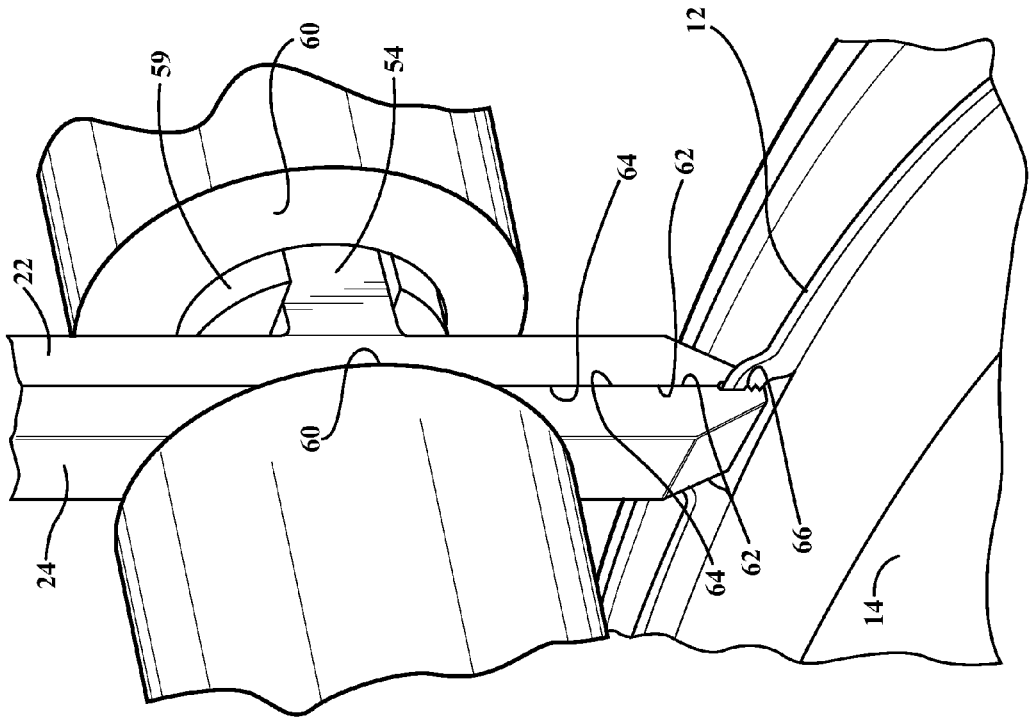
FIG. 9A is a view of the grip fingers of FIG. 9 shown pulling the seal lip.
Figure 9:
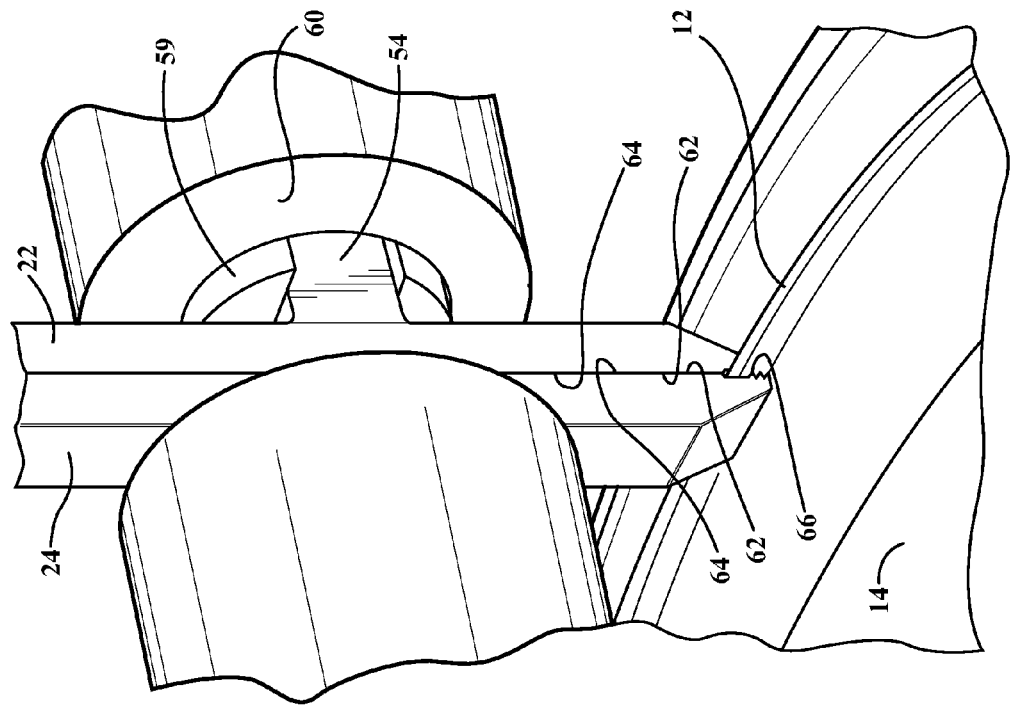
FIG. 9 is an enlarged view showing a pair of grip fingers clamped to a seal lip of the seal of FIG. 3.

To facilitate clamping the seal lip 12 in a manner that does not adversely affect or otherwise damage the seal lip 12, as best shown in FIG. 8E, the clamping fingers 22, 24 have first clamping surfaces 62 extending immediately adjacent the free end 58, wherein the first clamping surfaces 62 are recessed a distance (d) relative to an adjacent second surface 64 of the fingers 22, 24 extending toward the coupler 54 and the other free end 56 from the first clamping surface 62. As such, while clamping the seal lip 12, the "raised" second surfaces 64 are free to abut one another while the recessed first clamping surfaces 62 remained laterally spaced from one another by a predetermined gap distance which is two times the recessed distance (2d). The gap distance 2d can be controlled as desired by controlling the recessed depth d of the first clamping surfaces 62, depending on the seal lip dimensions and material type. To further facilitate gripping the seal lip 12 during testing, the recessed surfaces 62 can be formed having a plurality of undulating or serrated projections, also referred to as teeth 66. It should be recognized that the teeth 66 extend between peaks P and valleys V, wherein the peaks P remain spaced from one another a minimum distance of 2d given the teeth 66 are formed in the recessed first clamping surfaces 62. The teeth 66, aside from improving the gripping action, allow the material of the seal lip 12 to flow elastically within valleys V in addition to flowing within the gap between the fully clamped fingers 22, 24, thereby facilitating the avoidance of over compression and damage to the seal lip 12. The teeth 66 are shown as having undulating surfaces inclined generally 90 degrees relative to one another and extending between opposite sides of the clamping fingers 22, 24, though it should be recognized that the teeth could be formed having undulating surfaces inclined otherwise. In addition, it should be recognized that the clamping fingers 22, 24 can be sized accordingly (width and length), depending on the size of the seal being tested.

In use, with the seal 16 operably fixed to the support plate 30, the clamping fingers 22, 24 are positioned on opposite sides of the seal lip 12 to be tested. In the embodiment shown, the clamping fingers 22, 24 are lowered via controlled telescoping movement the pulling member 32, though it should be recognized that the support base 35 could also be configured for movement, if desired. With the clamping fingers 22, 24 located in their desired position, the clamping fingers 22, 24 are then moved laterally toward one another via controlled movement of the moveable plungers/pistons 59 within the piston members 60, such as via pneumatic pressure, hydraulic pressure, or otherwise. The clamping fingers 22, 24 are moved into predetermined clamping pressure with the seal lip 12, wherein at this time the second surfaces 64 of the fingers 22, 24 could be brought into abutment with one another as there is no seal lip material between the second surfaces 64. As discussed, the recessed first clamping surfaces 62 remain spaced from one another by a minimum distance 2d given the offset heights between the first and second surfaces 62, 64. Then, upon bringing the clamping fingers 22, 24 into their desired clamped relation with the seal lip 12, the pulling member 32 is telescopically actuated to cause the clamping fingers 22, 24 to pull axially along the direction of the axes 18, 20, thereby imparting a tensile pulling force along the seal lip axis 20. The pulling force is monitored and recorded via suitable force indicating sensors and recording apparatus until the test is completed.

While conducting the tensile test, one of two primary results will occur. Firstly, the seal lip 12 will tear, such as at location 1 shown in FIG. 10, thus leaving some seal lip material fixed to the case 14, or secondly, the material of the seal lip 12 will separate from the case 14, such as at location 2 shown in FIG. 10. In either case, the force required to achieve the result is monitored and recorded. Generally, if the seal lip 12 peals away from the case 14 at location 2, it is an indication that the mechanism used to bond the seal lip 12 to the case 14 is the weak link. Otherwise, if the seal lip 14 tears at location 1, the tensile strength of the seal lip material is the weak link. Then, upon completing the initial testing on the seal lip 12 as described, the seal 16 can be repositioned angularly relative to the axis 18 to allow the clamping fingers 22, 24 to clamp onto an additional seal lip or lips extending along different axes, whereupon the same testing procedure as described can be performed. Accordingly, the apparatus 10 is useful for reliably and repeatedly testing the bond/fatigue strength of one or more seal lips extending along different angles relative to one another.

Many modifications and variations of the present invention are possible in light of the above teachings. It is, therefore, to be understood that the invention may be practiced otherwise than as specifically described, and that the scope of the invention is defined by any allowed claims related to this application.

What is claimed is:

1. A method of testing a bond or fatigue strength of a seal lip on a metal substrate, comprising:
    providing a seal assembly having a metal substrate with an elastomeric seal lip bonded thereto;
    operably fixing the seal assembly to a support plate and orienting a seal lip axis along which the seal lip extends to extend along a predetermined axis;
    clamping the seal lip between pair of clamping fingers without causing damage to the seal lip;
    pulling the seal lip with a force imparted by the clamping fingers along the predetermined axis until the seal lip either separates from the metal substrate or tears;
    providing each of the clamping fingers with a recessed clamping surface adjacent to a free end of the clamping fingers and a raised surface extending outwardly and away from the recessed clamping surface; and
    clamping the seal lip between the recessed clamping surfaces and bringing the raised surfaces into abutment with one another.

2. The method of claim 1 further including avoiding clamping the seal lip between the raised surfaces.

3. A method of testing a bond or fatigue strength of a seal lip on a metal substrate, comprising:
    providing a seal assembly having a metal substrate with an elastomeric seal lip bonded thereto:
    operably fixing the seal assembly to a support plate and orienting a seal lip axis along which the seal lip extends to extend along a predetermined axis;
    clamping the seal lip between pair of clamping fingers without causing damage to the seal lip;
    pulling the seal lip with a force imparted by the clamping fingers along the predetermined axis until the seal lip either separates from the metal substrate or tears; and
    providing the seal assembly with the seal lip axis extending in oblique relation to a central axis of the seal assembly.

4. An apparatus for testing at least one of a bond or fatigue strength of a seal lip, comprising:
    a tensile pulling mechanism; and
    a pair of clamping fingers having opposite free ends and a coupler member between said free ends, said couple member being operably attached to said tensile pulling mechanism, said clamping fingers having clamping surfaces adjacent at least one of said free ends and raised surfaces extending between said clamping surfaces and said coupler member, said clamping surfaces being recessed a first distance relative to said raised surfaces with said raised surfaces being free to abut one another upon said clamping fingers being clamped fully toward one another with said recessed clamping surfaces remaining laterally spaced from one another by a second distance that is two times said first distance.

5. The apparatus of claim 4 wherein said clamping surfaces have a plurality of undulating teeth.

6. The apparatus of claim 4 wherein said clamping fingers are configured and oriented to pull on the seal lip along an axis along which the seal lip extends.

* * * * *